United States Patent [19]

Boelema et al.

[11] Patent Number: 5,155,192
[45] Date of Patent: Oct. 13, 1992

[54] STABILIZED PEROXYDICARBONATE COMPOSITION

[75] Inventors: Eltjo Boelema, Bathmen; Martinus C. Tammer, Diepenveen; Johan Nuysink, Rijssen, all of Netherlands

[73] Assignee: Akzo N.V., Netherlands

[21] Appl. No.: 219,898

[22] Filed: Jul. 14, 1988

Related U.S. Application Data

[63] Continuation of Ser. No. 911,132, Sep. 24, 1986, abandoned.

[30] Foreign Application Priority Data

Oct. 30, 1985 [NL] Netherlands .......................... 8502957

[51] Int. Cl.⁵ .............................. C08F 4/38; C08F 4/32
[52] U.S. Cl. .................................... 526/228; 526/230; 526/230.5
[58] Field of Search ...................... 526/228, 230, 230.5

[56] References Cited

U.S. PATENT DOCUMENTS

| | | | |
|---|---|---|---|
| 2,491,397 | 12/1949 | Stevens | 526/228 X |
| 3,634,379 | 1/1972 | Hauser | 526/228 |
| 3,687,867 | 8/1972 | Lewis et al. | 252/426 |
| 3,778,422 | 12/1973 | Farber | 526/228 |
| 4,396,737 | 8/1983 | Leatherman | 524/176 |
| 4,440,885 | 4/1984 | Tamosauskas | 252/186.26 |

OTHER PUBLICATIONS

Strain et al J.A.C.S. Mar. 1950 vol. 72 pp. 1254–1263.
Chemical Abstracts, vol. 85, 1976, p. 91, 179236.

*Primary Examiner*—Thurman K. Page
*Assistant Examiner*—Peter F. Kulkosky
*Attorney, Agent, or Firm*—Oliff & Berridge

[57] ABSTRACT

This disclosure relates to storageable and/or transportable compositions containing a peroxydicarbonate to which an organic hydroperoxide, e.g. t-butyl hydroperoxide, has been added. The hydroperoxide serves to retard peroxydicarbonate decomposition. The compositions may be in the form of physical mixtures, aqueous dispersions or solutions in organic solvents.

13 Claims, No Drawings

STABILIZED PEROXYDICARBONATE COMPOSITION

This is a continuation of application Ser. No. 06/911,132 filed Sep. 24, 1986, now abandoned.

The invention relates to a storageable and/or transportable composition containing a peroxydicarbonate to which a hydroperoxide of the general formula ROOH has been added.

A composition of the type indicated above is disclosed in the Journal of the American Chemical Society, Volume 72, pp. 1254-1263 (1950). This publication describes the preparation of a number of peroxydicarbonates and mentions that the decomposition of diisopropyl peroxydicarbonate is retarded by the addition thereto of substances such as iodine, phenol, hydroquinone, salicylic acid, nitromethane or pyrogallol; in this connection also mention is made of hydrogen peroxide (R=H in the afore-mentioned general formula) (p. 1261, at bottom of right hand column).

In actual practice, however, there are several disadvantages to the use of hydrogen peroxide as stabilizing agent serving to retard the decomposition of peroxydicarbonates. In the first place, hydrogen peroxide cannot very well be used in aqueous emulsions or suspensions of peroxydicarbonates in that it has been found that the hydrogen peroxide present therein is entirely or practically entirely in the aqueous phase, as a result of which its stabilizing action in the organic peroxydicarbonate phase is nil or only very small. In the second place, its use in non-aqueous systems, as in peroxydicarbonates as such or in peroxydicarbonates dissolved in organic solvents, has met with problems in actual practice in that it has been found extremely difficult for sufficiently high concentrations of hydrogen peroxide to be reproducibly mixed into these systems or to be dissolved in such a way that their distribution is permanently homogeneous. In the third place, hydrogen peroxide is extremely susceptible to decomposition induced by traces of metal ions, as a result of which its use as stabilizing agent is considerably restricted. It is true that this metal ion induced decomposition may be restrained by adding sequestering agents, such as EDTA, dipicolinic acid and certain tin compounds. Within the scope of the present application, however, this leads to undesirable contamination of the endproduct.

It has now been found that as compared with hydrogen peroxide organic hydroperoxides display an at least equivalent, if not better, stabilizing action, without showing the above-described disadvantages attached to the use of hydrogen peroxide.

The composition according to the invention is characterized in that R represents an organic group and the amount of hydroperoxide is at least 0.03 equivalent percent, calculated on the peroxydicarbonate.

It should be noted that U.S. Pat. No. 4,515,929 describes aqueous dispersions of organic peroxides, including peroxydicarbonates, which contain diphenyl peroxydicarbonate or a di(alkyl substituted)phenyl peroxydicarbonate as stabilizing agent. These stabilizing agents, however, have the disadvantage that they may give rise to the formation of coloured products. Moreover, for certain purposes the use of aromatic compounds may be objectionable.

It should also be noted that U.S. Pat. No. 3,778,422 discloses aqueous polymerization mixtures containing a vinyl halide monomer and, based on the weight of the monomer component, 0.005 to 1% of a peroxydicarbonate and 0.00001 to 0.1% of an alkyl hydroperoxide having 2 to 8 carbon atoms. In these mixtures the hydroperoxide serves to eliminate or substantially reduce the tendency of vinyl halides to undergo heat kicks when they are polymerized in aqueous systems in the presence of a peroxydicarbonate initiator. Unlike the compositions of the present invention such polymerization mixtures, of course, are not storageable and/or transportable. Furthermore, it should be noted that the compositions of the present invention do not contain vinyl halide monomers.

The peroxydicarbonates stabilized according to the invention are well-known compounds of which many are commercially available. They are used as initiators in the mass, emulsion or suspension polymerization of ethylenically unsaturated compounds. The peroxydicarbonates are of the general structural formula:

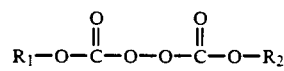

wherein $R_1$ and $R_2$ represent organic groups. $R_1$ and $R_2$ generally each have 1 to 20 carbon atoms, preferably 2 to 18 carbon atoms, and more particularly 2 to 16 carbon atoms. Preferably, $R_1$ and $R_2$ represent branched or non-branched, substituted or unsubstituted alkyl, alkenyl or cycloalkyl groups. As suitable substituents may be mentioned aromatic groups, halogen atoms, such as chlorine and bromine, nitro groups, aryloxy groups and alkoxy groups. As examples of $R_1$ and $R_2$ may be mentioned methyl, ethyl, n-propyl, isopropyl, n-butyl, sec.-butyl, isobutyl, hexyl, octyl, 2-ethylhexyl, lauryl, mirystyl, cetyl, stearyl, allyl, methallyl, crotyl, cyclohexyl, 4-t-butylcyclohexyl, 4-t-amylcyclohexyl, benzyl, 2-phenylethyl, 2-phenylbutyl, 2-phenoxyethyl, 2-methoxyethyl, 2-ethoxyethyl and 3-methoxybutyl. Although $R_1$ and $R_2$ are generally identical, the invention is not limited to these symmetric peroxydicarbonates. Also stabilized by using the present hydroperoxides are asymmetric peroxydicarbonates, such as isopropyl-sec.-butyl peroxydicarbonate, mixtures of symmetric peroxydicarbonates and mixtures of symmetric and asymmetric peroxydicarbonates, such as the mixtures of diisopropyl peroxydicarbonate, di-sec.butyl peroxydicarbonate and isopropylsec.butyl peroxydicarbonate described in U.S. Pat. No. 4,269,726.

The preparation of the peroxydicarbonates is carried out in the usual manner by reacting a chloroformate with hydrogen peroxide in the presence of aqueous sodium hydroxide at low temperature (e.g. 0°-20° C.), as described in, for instance, U.S. Pat. No. 2,370,588, EP 49470 B1 and in the above-mentioned article in Journal of the American Chemical Society.

The hydroperoxides which according to the invention are used as stabilizing agent are also well-known compounds, many of which are commercially available. They are of the general formula:

ROOH wherein R represents an organic group, but more particularly a branched or non-branched, substituted or unsubstituted alkyl group, alkenyl group, alkynyl group or cycloalkyl group. R generally does not have more than 40 carbon atoms, preferably not more than 20 carbon atoms and more particularly not more than 12 carbon atoms. As examples of suitable substituents may be mentioned the hydroperoxy group, the phenyl group and the hydroxyl group. Examples of hydroperoxides include methyl hydroperoxide, ethyl hydroperoxide, n-propyl hydroperoxide, isopropyl hydroperoxide, sec.-butyl hydroperoxide, isobutyl hydroperoxide, 1-phenyl-1-hydroperoxy ethane, benzyl hydroperoxide, methylethyl ketone peroxide (i.e. a mixture of 2,2'-dihydroperoxy-2-2'-di-n-butyl peroxide and 2,2-dihydroperoxy butane), cyclohexanone peroxide (i.e. a mixture of 1,1'-dihydroperoxy-1,1'-dicyclohexyl peroxide and 1,1-dihydroperoxy cyclohexane) and cyclohexyl hydroperoxide. It is preferred that use should be made of tertiary hydroperoxides, i.e. hydroperoxides having one or more hydroperoxy groups linked to tertiary carbon atoms. As examples of such preferred hydroperoxides may be mentioned t-butyl hydroperoxide, t-amyl hydroperoxide, 2-hydroperoxy-2-methyl pentane, 2-hydroperoxy-2-methyl-3-butene, 2-hydroperoxy-2,4,4-trimethyl pentane, 2,5-dihydroperoxy-2,5-dimethyl hexane, 2,5-dihydroperoxy-2,5-dimethyl-3-hexyn, 2,6-dihydroperoxy-4-hydroxy-2,6-dimethyl heptane, 2-hydroperoxy-4-hydroxy-2-methyl butane, 2-hydroperoxy-4-hydroxy-2-methyl pentane, 2-hydroperoxy-4-hydroxy-2-methyl heptane, 3-ethyl-3-hydroperoxy-5-hydroxy hexane, cumyl hydroperoxide (2-phenyl-2-hydroperoxy propane), m- and p-isopropyl cumyl hydroperoxide, 1-hydroperoxy-1-methyl cyclohexane, 1-hydroperoxy-5-hydroxy-1,3,3-trimethyl cyclohexane, p-menthane hydroperoxide and pinane hydroperoxide. According to the invention use may also be made of mixtures of hydroperoxides as stabilizing agent.

The hydroperoxides may be prepared by prior art methods as described in, for instance, U.S. Pat. No. 2,845,461, NL 6 713 241, U.S. Pat. No. 3,049,477, U.S. Pat. No. 2,954,405, U.S. Pat. No. 3,592,857, U.S. Pat. No. 3,475,498, U.S. Pat. No. 4,154,768 and U.S. Pat. No. 2,996,549.

The amount of hydroperoxide in the composition according to the invention is generally at least 0.03 equivalent percent, preferably at least 0.05 equivalent percent, more particularly at least 0.07 equivalent percent, and even more particularly at least 0.10 equivalent percent, calculated on the peroxydicarbonate. By equivalent percent is to be understood here:

$$\frac{\text{number of gram atoms of active oxygen in the hydroperoxy group(s) of the added ROOH}}{\text{number of gram molecules of peroxydicarbonate}} \times 100\%$$

Adding less than 0.03 equivalent percent results in insufficient stabilization. The upper limit of the amount of hydroperoxide to be used is governed by practical considerations. Although the amount used may be as high as 3.5 equivalent percent, amounts of that order or even higher percentages do not enhance the stabilizing effect; moreover, such amounts may impair the final use of the peroxydicarbonate. In general, the composition according to the invention therefore does not contain more than 3 equivalent percent, preferably not more than 2.5 equivalent percent, and more particularly not more than 2 equivalent percent of hydroperoxide, calculated on the peroxydicarbonate.

The compositions according to the invention may be divided into (i) physical mixtures as such, in the form of liquids, granules, powders or flakes, (ii) dispersions and (iii) solutions. The wording physical mixture as such used here refers to a mixture of pure, or virtually pure, peroxydicarbonate and hydroperoxide. By the term dispersion is to be understood here a peroxydicarbonate (discontinuous phase) dispersed in a liquid (continuous phase), the hydroperoxide being entirely or at least substantially in the discontinuous peroxydicarbonate phase and by a solution is to be understood here a homogeneous mixture of an organic solvent, peroxydicarbonate and hydroperoxide.

The preparation of a physical mixture according to the invention may be effected in a simple manner by mixing a peroxydicarbonate with the desired amount of hydroperoxide in a conventional mixing apparatus and, if desired, granulating, pulverizing or flaking the resulting mixture (route 1). However, in order that the greatest possible benefit may be derived from the stabilizing effect of the hydroperoxide and the two components may be mixed as homogeneously as possible, it is preferred that the hydroperoxide either be added to the respective chloroformate-containing reaction mixture before the preparation of the peroxydicarbonate (route 2) or be added to the unprocessed reaction mixture immediately after the preparation of the peroxydicarbonate (route 3). The option for route 2 or route 3 will depend, int.al., on the reactivity of the hydroperoxide toward the chloroformate. For, the formation of peroxymonocarbonates at the expense of the hydroperoxide should of course be avoided.

When use is made of route 2 or 3, it will not be difficult for a man skilled in the art so to choose the amount of hydroperoxide to be added that, taking account of possible losses of hydroperoxide in the aqueous phase, which is known to be generally alkaline, the physical mixture of peroxydicarbonate and hydroperoxide finally to be obtained will contain the amount of hydroperoxide desired.

A dispersion according to the invention can be prepared in a simple manner, use being made of the emulsifiers and/or colloids and of the apparatus known to be employed in such preparations, by dispersing a physical mixture according to the invention (see above) or by adding the desired amount of hydroperoxide, with vigorous mixing, to a peroxydicarbonate dispersion known from the state of the art. A detailed description of the state of the art with regard to peroxydicarbonate dispersions and their preparation is given among other places, in NL 8 000 260, EP 42 826, U.S. Pat. No. 3,825,509, U.S. Pat. No. 3,988,261, U.S. Pat. No. 4,092,470 and U.S. Pat. No. 4,515,929. By dispersions are to be understood both emulsions (i.e. dispersions of liquid peroxydicarbonates) and suspensions (i.e. dispersions of solid peroxydicarbonates). The dispersions according to the invention generally contain 5 to 70% by weight, preferably 15 to 70% by weight of peroxydicarbonate. As dispersion medium generally water is used. To reduce the freezing point of the dispersions 2 to 20% by weight of an alkanol having 1 to 4 carbon atoms and/or an alkane diol having 2 to 4 carbon atoms may be added to them. See, for example, EP 32 757.

Solutions according to the invention may contain the organic solvents normally employed for peroxydicarbonate solutions. As examples of such solvents may be mentioned esters of phthalic acid, such as dibutyl phthalate, and aliphatic and aromatic hydrocarbons, such as hexane, mineral oil, benzene, toluene, the xylenes and (iso)paraffins, such as isododecane. As very suitable solvents may also be mentioned monomers containing activated allyl groups, such as diethylene glycol bis(allyl carbonate), which monomer is used in the manufacture of plastics lenses.

The preparation of a solution according to the invention may be effected by adding the amount of hydroperoxide desired to a peroxydicarbonate solution known from the state of the art or by dissolving a physical mixture according to the invention (see above) in an organic solvent or mixing it with such a solvent. In some cases solutions according to the invention also may be prepared by using methods similar to those described in Japanese Patent Application prepublished under No. 55 139 357, where the solvent to be used forms part of the chloroformate-containing reaction mixture. It will be clear that also in this case, depending on the reactivity of the hydroperoxide toward the chloroformate, the hydroperoxide is added to the chloroformate-containing mixture either before the preparation of the peroxydicarbonate or is added to the unprocessed reaction mixture immediately after said preparation and that in the choice of the amount of hydroperoxide to be used allowance should be made for possible losses in the aqueous phase. Solutions according to the invention generally contain at least 3% by weight, but preferably at least 10% by weight of peroxydicarbonate. The upper limit of the amount of peroxydicarbonate is governed by practical considerations, which have to do, int. al., with the solubility of the peroxydicarbonate in the solvent to be used.

The compositions according to the invention generally display excellent storage stability, which is due to the presence therein of a hydroperoxide. As compared with the corresponding, non-stabilized peroxydicarbonates or peroxydicarbonate formulations they can be stored for a longer time at their recommended storage temperature without loss of quality. Moreover, in the case of peroxydicarbonates or peroxydicarbonate formulations which are normally stored at a low temperature (e.g., −15° C.), higher storage and transport temperatures are now allowed.

The compositions according to the invention are suitable to be used in the mass, emulsion or suspension (co)polymerization of ethylenically unsaturated compounds. As examples of ethylenically unsaturated compounds may be mentioned vinyl chloride, styrene, ethylene, vinyl acetate, diethylene glycol bis(allyl carbonate), acrylic acid, acrylic acid esters, methacrylic acid and methacrylic acid esters. The composition according to the invention is generally used in an amount such that at the start of the reaction peroxydicarbonate is present in an amount of 0.01 to 3% by weight, calculated on the monomer.

Finally, it should be noted that in the compositions according to the invention there may, in addition to a peroxydicarbonate, be present other initiating peroxides, such as dilauroyl peroxide or acetylcyclohexane sulphonyl peroxide. Combinations of such so-called rapid and so-called slow initiators are often used in actual practice in order to obtain constant reaction speeds throughout the polymerization reactions. See, for example, U.S. Pat. No. 3,781,255.

The invention will be further described in the following examples.

EXAMPLE 1

In a so-called adiabatic test the time is measured which it takes for a peroxide sample heated to a particular temperature before it starts to undergo uncontrolled thermal decomposition; this decomposition manifests itself by an exponentially increasing temperature of the sample. In all the experiments the same apparatus was used in order to permit comparison of the results obtained.

In this example the stabilizing effect has been determined of 2-hydroperoxy-2,4,4-trimethyl pentane (HTMP) on dimyristyl peroxydicarbonate (Exp. 1-4 to 1-12) and dicetyl peroxydicarbonate (Exp. 1-17 to 1-20). The experiments were carried out as follows.

To about 72 g of entirely or partly molten peroxydicarbonate there was added, with stirring, the desired amount of hydroperoxide. The resulting mixture was rapidly transferred to a Dewar vessel, which was closed with a rubber stopper. Of the mixture, which was magnetically stirred, the starting temperature was registered with the aid of an Ni-Cr-Ni thermocouple projecting into the mixture through a passage in the rubber stopper. Subsequently, the time it took for the mixture to decompose was measured.

The compositions and the results are given in Table 1, which also mentions the results of comparative experiments (1-1 to 1-3, 1-13 to 1-16) where no hydroperoxide was contained in the samples. The results clearly show that the presence of hydroperoxide retards the decomposition of the peroxydicarbonates.

TABLE 1

| Exp. | Peroxydi-carbonate | HTMP (equiv. %) | Starting temperature (°C.) | Time up to decomposition (min.) |
|---|---|---|---|---|
| 1-1 | dimyristyl | 0 | 45.8 | 3.9 |
| 1-2 | " | 0 | 46.1 | 3.2 |
| 1-3 | " | 0 | 48.3 | 2.2 |
| 1-4 | " | 0.70 | 47.5 | 11.0 |
| 1-5 | " | 0.63 | 48.3 | 7.3 |
| 1-6 | " | 0.66 | 56.8 | 2.0 |
| 1-7 | " | 1.58 | 44.4 | 35.0 |
| 1-8 | " | 1.58 | 46.1 | 24.7 |
| 1-9 | " | 1.58 | 50.5 | 10.8 |
| 1-10 | " | 1.58 | 55.6 | 4.3 |
| 1-11 | " | 3.48 | 47.1 | 28.5 |
| 1-12 | " | 3.52 | 53.4 | 13.3 |
| 1-13 | dicetyl | 0 | 51.2 | 2.7 |
| 1-14 | " | 0 | 55.2 | 2.5 |
| 1-15 | " | 0 | 57.6 | 1.6 |
| 1-16 | " | 0 | 60.5 | 1.4 |
| 1-17 | " | 1.33 | 53.2 | 9.8 |
| 1-18 | " | 1.48 | 58.0 | 4.3 |
| 1-19 | " | 3.71 | 54.1 | 17.0 |
| 1-20 | " | 3.71 | 59.0 | 7.2 |

EXAMPLE 2

Use being made of the same procedure as described in Example 1, adiabatic tests were carried out with the compositions given in Table 2. The experiments 2-1, 2-19 and 2-21 are comparative experiments on the peroxydicarbonates as such; all the other experiments concern compositions according to the invention in the form of physical mixtures. In the Experiments 2-1 to 2-18 the time (heating time t) was measured which the sample took to be heated from 15° to 30° C. In the experiments 2-19 to 2-22 the starting temperature was 10° C. and also a final temperature of 30° C. was adhered to.

The results are given in Table 2. These results clearly show the retarding effect of the various hydroperoxides on the decomposition of peroxydicarbonates.

TABLE 2

| Exp. | Peroxy-dicarbonate | Hydroperoxide | Amount of hydroperoxide (equiv. %) | Heating time t (h) |
| --- | --- | --- | --- | --- |
| 2-1 | EH[1] | — | — | 3.5 |
| 2-2 | " | TBHP[4] | 0.10 | 9 |
| 2-3 | " | " | 0.19 | 12 |
| 2-4 | " | " | 0.38 | 25.5 |
| 2-5 | " | " | 0.77 | 50 |
| 2-6 | " | " | 1.92 | >120 |
| 2-7 | " | CHP[5] | 0.77 | 46.5 |
| 2-8 | " | TAHP[6] | 0.77 | 55.5 |
| 2-9 | " | HTMP[7] | 0.77 | 60 |
| 2-10 | " | IBHP[8] | 0.77 | >25 |
| 2-11 | " | SBHP[9] | 1.92 | 114.5 |
| 2-12 | " | CHHP[10] | 0.36 | 7.5 |
| 2-13 | " | MEKP[11] | 0.45 | 18 |
| 2-14 | " | HGHP[12] | 1.42 | 19 |
| 2-15 | " | TPHP[13] | 1.60 | 69 |
| 2-16 | " | THHP[14] | 1.81 | 110 |
| 2-17 | " | PMHP[15] | 1.42 | 111.5 |
| 2-18 | " | MICH[16] | 1.10 | 53.5 |
| 2-19 | SB[2] | — | — | 20 |
| 2-20 | " | TBHP[4] | 0.52 | 59 |
| 2-21 | MIX[3] | — | — | 4 |
| 2-22 | " | TBHP[4] | 0.49 | 35 |

[1] di-2-ethylhexyl peroxydicarbonate
[2] di-sec.butyl peroxydicarbonate
[3] a mixture (1:1:2) of diisopropyl peroxydicarbonate, di-sec.butyl peroxydicarbonate and isopropyl-sec.butyl peroxydicarbonate
[4] t-butyl hydroperoxide
[5] cumyl hydroperoxide
[6] t-amyl hydroperoxide
[7] 2-hydroperoxy-2,4,4-trimethyl pentane
[8] isobutyl hydroperoxide
[9] sec.butyl hydroperoxide
[10] cyclohexanone peroxide
[11] methylethyl ketone peroxide
[12] 2-hydroperoxy-4-hydroxy-2-methyl pentane
[13] 2-hydroperoxy-2-methyl-3-butene
[14] 2-hydroperoxy-2-methyl pentane
[15] p-menthane hydroperoxide
[16] m-isopropyl cumyl hydroperoxide

EXAMPLE 3

Use being made of the same procedure as described in Example 2, experiments were conducted on solutions of di-2-ethylhexyl peroxydicarbonate in isododecane and in dibutylphthalate. The solutions contained 65 and 75% by weight of peroxydicarbonate, respectively. The compositions also contained a hydroperoxide as given in Table 3. Experiments 3-1 and 3-5 are comparative experiments. In all the experiments the time was measured which the sample took to be heated from 20° C. to 35° C.

The results are mentioned in Table 3, These data clearly show that also the decomposition of peroxydicarbonates in the dissolved state is retarded by the presence of hydroperoxides.

TABLE 3

| Exp. | Solvent | Hydroperoxide | Amount of hydroperoxide (equiv. %) | Heating time t (h) |
| --- | --- | --- | --- | --- |
| 3-1 | isododecane | — | — | 4.2 |
| 3-2 | " | HTMP[1] | 0.29 | 6.3 |
| 3-3 | " | " | 0.58 | 11.3 |
| 3-4 | " | " | 1.17 | 21.9 |
| 3-5 | dibutylphthalate | — | — | 2.7 |
| 3-6 | " | TBHP[2] | 1.02 | 26 |

[1] 2-hydroperoxy-2,4,4-trimethyl pentane
[2] t-butyl hydroperoxide

EXAMPLE 4

Use being made of the same procedure as described in Example 2, experiments were conducted on aqueous emulsions of di-2-ethylhexyl peroxydicarbonate. To emulsions containing 40% by weight of the peroxydicarbonate, 3% by weight of polyvinyl alcohol (Gohsenol ® KP-08, a commercial product of Nippon Gohsei), 20% by weight of methanol and water, there was added, with stirring, a hydroperoxide as given in Table 4. Experiment 4-1 is a comparative experiment. In all the experiments the time was measured which it took for the composition to be heated from 19° C. to a temperature of 28° C.

The results are mentioned in Table 4. These data clearly show that also the decomposition of peroxydicarbonates in emulsified form is retarded by the presence of hydroperoxides.

TABLE 4

| Exp. | Hydroperoxide | Amount of hydroperoxide (equiv. %) | Heating time t (h) |
| --- | --- | --- | --- |
| 4-1 | — | — | 3 |
| 4-2 | TBHP[1] | 0.38 | 6.5 |
| 4-3 | TBHP[1] | 0.96 | 23.5 |
| 4-4 | HTMP[2] | 0.41 | 10.5 |

[1] t-butyl hydroperoxide
[2] 2-hydroperoxy-2,4,4-trimethyl pentane

EXAMPLE 5

Use being made of the same procedure as described in Example 2, experiments were conducted on aqueous suspensions of dimyristyl peroxydicarbonate (di-$C_{14}$), dicetyl peroxydicarbonate (di-$C_{16}$) and di(4-t-butyl cyclohexyl) peroxydicarbonate (di-TBCH).

The preparation of the suspensions was as follows. Use was made of suspensions containing 40% by weight of peroxydicarbonate and prepared by using a mixture of two emulsifiers, which are both ethoxylated nonyl phenols. The suspensions were of the following composition:

| Peroxide | Emulsifier with HLB = 10 (wt %) | Emulsifier with HLB = 14.5 (wt %) |
| --- | --- | --- |
| di-$C_{14}$ | 1 | 2 |
| di-$C_{16}$ | 2 | 2 |
| di-TBCH | 0.5 | 1 |

To these suspensions there was added, with stirring, an amount of hydroperoxide as indicated in Table 5. Experiments 5-1, 5-4 and 5-7 are comparative experiments. In the experiments 5-1 to 5-6 the heating time was measured which it took for the compositions to be heated from 30° C. to a temperature of 60° C. In the remaining three experiments the starting temperature and the final temperature were 56° C. and 72° C., respectively.

The results are given in Table 5. These data clearly show that also in suspensions the decomposition of peroxydicarbonates is retarded by the presence of hydroperoxides.

TABLE 5

| Exp. | Peroxydicarbonate | Hydroperoxide | Amount of hydroperoxide (equiv. %) | Heating time t (h) |
| --- | --- | --- | --- | --- |
| 5-1 | di-$C_{14}$ | — | — | 11.8 |
| 5-2 | " | HTMP[1] | 1.40 | 20.9 |
| 5-3 | " | TBHP[2] | 2.85 | 23.5 |
| 5-4 | di-$C_{16}$ | — | — | 18.5 |

TABLE 5-continued

| Exp. | Peroxydi-carbonate | Hydro-peroxide | Amount of hydroperoxide (equiv. %) | Heating time t (h) |
|---|---|---|---|---|
| 5-5 | " | HTMP[1] | 1.56 | 33.3 |
| 5-6 | " | TBHP[2] | 3.16 | 31.8 |
| 5-7 | di-TBCH | — | — | 4.0 |
| 5-8 | " | HTMP[1] | 1.09 | 7.5 |
| 5-9 | " | TBHP[2] | 2.21 | 7.4 |

[1]2-hydroperoxy-2,4,4-trimethyl pentane
[2]t-butyl hydroperoxide

EXAMPLE 6

In this example the effect of the presence of hydroperoxide on the storage stability of di-2-ethylhexyl peroxydicarbonate is determined. Samples of this peroxydicarbonate with and without t-butyl hydroperoxide (TBHP) were stored at +5° C. and periodically examined for their peroxydicarbonate content.

The amounts of TBHP and the results are mentioned in Table 6. These data clearly show that the use of the present invention results in improved storage stability of the peroxydicarbonate.

TABLE 6

| Amount of TBHP (equiv. %) | Peroxydicarbonate content (%) | | | |
|---|---|---|---|---|
| | start | 12 days | 15 days | 29 days |
| — | 99.8 | 71.0 | 65.0 | 46.8 |
| 0.19 | 99.8 | 99.3 | 98.8 | 82.4 |
| 1.92 | 99.8 | 99.8 | 99.1 | 97.7 |

EXAMPLE 7

The self accelerating decomposition temperature (SADT) of di-2-ethylhexyl peroxydicarbonate was determined by the method described in "Transport of Dangerous Goods, Recommendations of the Committee of Experts on the transport of dangerous goods; Chapter 11:11.9. Heat Accumulation Storage Test, 3rd revised edition, ST/SG/AC 10/1/Rev. 3; UN Publications, Sales No. E. 83. VIII. I". See also in this publication "entry 2122" and Table 11.1. The SADT is an internationally accepted quantity which is determinative of the maximum temperature at which goods are allowed to be transported. The SADT of technically pure di-2-ethylhexyl peroxydicarbonate is 0° C. Adding 1.92 equivalent per cent of t-butyl hydroperoxide leads to an SADT of at least +15° C., which is additional evidence of the importance of the present invention.

EXAMPLE 8

A solution of 60% by weight of a mixture (1:1:2) of diisopropyl peroxydicarbonate, di-sec.butyl peroxydicarbonate and isopropyl-sec.butyl peroxydicarbonate in diethylene glycol bis(allyl carbonate) to which 0.81 equivalent per cent of t-butyl hydroperoxide (TBHP) had been added was tested for stability at −20° C. by determining the prepolymer formed in it after storage for 1 month and 2 months (use being made of High Performance Size Exclusion Chromatography) and the increase in viscosity (use being made of an Ubbelohde viscosity meter). For comparison also a solution containing no hydroperoxide was tested.

The results are given in Table 7. They clearly show the improved storage stability as a result of using the present invention.

TABLE 7

| Solution | Prepolymer (%)/Viscosity (cSt) | | |
|---|---|---|---|
| | start | 1 month | 2 months |
| no TBHP | 0/67.8 | 0.6/69.0 | 3.8/74.3 |
| with TBHP | 0/66.2 | <0.2/66.7 | 1.0/69.1 |

We claim:

1. A process for the (co) polymerization of ethylenically unsaturated compounds comprising:
    mixing a peroxydicarbonate and a hydroperoxide, thereby forming a composition consisting essentially of the peroxydicarbonate and the hydroperoxide, wherein the hydroperoxide is:
    1) of the formula ROOH, R representing an organic group having 40 or fewer carbon atoms;
    2) is present in an amount of at least 0.03 equivalent percent, calculated on the peroxydicarbonate; and
    3) is effective to enhance at least one of a storageability or transportability of the composition; and
    preparing the (co) polymerized ethylenically unsaturated compounds in the presence of the composition.

2. A composition consisting essentially of a peroxydicarbonate and a hydroperoxide of the formula ROOH, R representing an organic group having 40 or fewer carbon atoms, wherein said hydroperoxide is present in an amount of at least 0.03 equivalent percent, calculated on the peroxydicarbonate, and is effective to enhance the storageability and/or transportability of said composition.

3. A process for enhancing the storageability and/or transportability of a composition containing a peroxydicarbonate, comprising adding a peroxydicarbonate to a hydroperoxide of the formula ROOH, R representing an organic group having 40 or fewer carbon atoms, said hydroperoxide being present in an amount of at least 0.03 equivalent percent, calculated on the peroxydicarbonate, thereby forming a composition consisting essentially of said peroxydicarbonate and said hydroperoxide, the hydroperoxide being effective to enhance the storageability and/or transportability of the composition.

4. A composition according to claim 2, characterized in that the amount of hydroperoxide used is not more than 3.5 equivalent percent, calculated on the peroxydicarbonate.

5. A composition according to claim 2, characterized in that R represents a branched or non-branched, substituted or unsubstituted alkyl group, alkenyl group, alkynyl group or cycloalkyl group having not more than 40 carbon atoms.

6. A composition according to claim 5, characterized in that the hydroperoxide is a tertiary hydroperoxide.

7. A composition according to claim 6, characterized in that the hydroperoxide is selected from the group consisting of:
   t-butyl hydroperoxide,
   t-amyl hydroperoxide,
   2-hydroperoxy-2-methyl pentane,
   2-hydroperoxy-2,4,4-trimethyl pentane,
   cumyl hydroperoxide and
   p-menthane hydroperoxide.

8. A composition according to claim 2, characterized in that the peroxydicarbonate satisfies the general structural formula

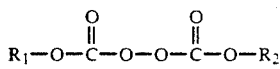

wherein $R_1$ and $R_2$ have the meaning of branched or non-branched, substituted or unsubstituted alkyl groups, alkenyl groups or cycloalkyl groups.

9. A composition according to claim 8, characterized in that the peroxydicarbonate is selected from the group consisting of:
di-n-propyl peroxydicarbonate,
diisopropyl peroxydicarbonate,
di-n-butyl peroxydicarbonate,
di-sec.butyl peroxydicarbonate,
a mixture of diisopropyl peroxydicarbonate, di-sec.butyl peroxydicarbonate and isopropyl-sec.butyl peroxydicarbonate,
di-2-ethylhexyl peroxydicarbonate,
di-3-methoxybutyl peroxydicarbonate,
di-2-phenoxyethyl peroxydicarbonate,
dimyristyl peroxydicarbonate,
dicetyl peroxydicarbonate,
dicyclohexyl peroxydicarbonate and
di(4-t-butyl cyclohexyl) peroxydicarbonate.

10. A composition according to claim 2, characterized in that the composition is formulated in the form of a physical mixture.

11. A composition according to claim 2, characterized in that the composition is formulated in the form of an aqueous dispersion.

12. A composition according to claim 2, characterized in that the composition is formulated in the form of a solution in an organic solvent.

13. A composition according to claim 12, characterized in that the organic solvent is selected from the group consisting of:
(iso)paraffins, phthalic acid esters and
diethylene glycol bis(allyl)carbonate.

* * * * *